United States Patent [19]

Whitten

[11] 4,304,483
[45] Dec. 8, 1981

[54] HAND-HELD RETINA PHOTOGRAPHING APPARATUS

[76] Inventor: Mark E. Whitten, 200 N. Pickett St., #107, Alexandria, Va. 22304

[21] Appl. No.: 103,358

[22] Filed: Dec. 13, 1979

[51] Int. Cl.³ .............................................. G03B 17/56
[52] U.S. Cl. ..................................... 354/293; 354/62; 351/38
[58] Field of Search ....................... 354/81, 82, 62, 79, 354/293, 126; 351/6, 7, 16, 38

[56] References Cited

U.S. PATENT DOCUMENTS

| | | | |
|---|---|---|---|
| 2,292,044 | 8/1942 | Bucky | 354/126 |
| 2,403,892 | 7/1946 | McFarlane et al. | 354/126 |
| 2,459,418 | 1/1949 | Ellis | 354/126 X |
| 2,483,711 | 10/1949 | Roos | 354/293 |
| 3,914,032 | 10/1975 | Takand et al. | 354/62 X |

*Primary Examiner*—John Gonzales
*Attorney, Agent, or Firm*—Maky, Renner, Otto & Boisselle

[57] ABSTRACT

An apparatus for use in photographing the eye is conveniently hand-held for true portability and is adaptable for usage in conjunction with that equipment ordinarily available in the ophthalmologist's office. The apparatus includes a support for holding in relatively fixed positions and in a secure manner an indirect lens for forming an image of the area to be photographed, a camera for viewing and photographing such image, an aligning mounting bracket for positioning the viewing sight of an indirect ophthalmoscope in correct optical alignment relative to the support and relative to the optical axis of the camera so as to illuminate the object or area to be viewed, and a beam splitter for directing the image light to the camera and passing illuminating light from the indirect ophthalmoscope to the object.

13 Claims, 4 Drawing Figures

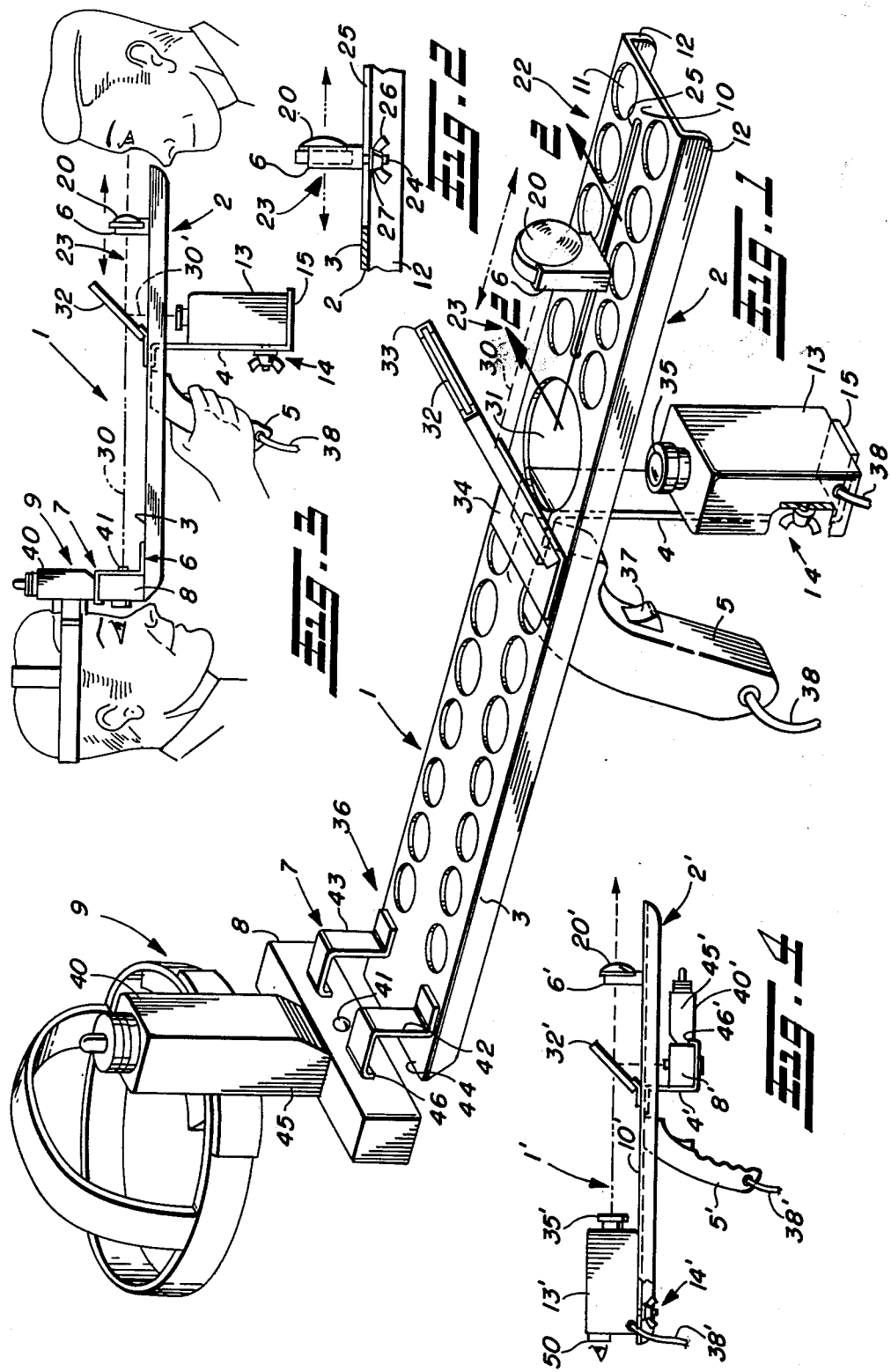

HAND-HELD RETINA PHOTOGRAPHING APPARATUS

BACKGROUND OF THE INVENTION

The present invention relates generally, as indicated, to an apparatus for facilitating taking photographs of the retina, other parts of the eye, and the like, and, more particularly, relates to such an apparatus that may be hand-held for true portability.

Photographs of the retina and other parts of the eye or the like are frequently used by ophthalmologists as a tool facilitating examination, as is disclosed, for example, in U.S. Pat. No. 4,018,514. In the past the equipment used to take such photographs has been relatively expensive, requiring specially manufactured, relatively sophisticated optical and photographing instruments, and has been relatively bulky, for example to the extent that the equipment is not readily portable.

SUMMARY OF THE INVENTION

In accordance with the present invention a hand-held retina photographing apparatus provides a means by which that sophisticated equipment ordinarily conveniently available to an ophthalmologist, such as a conventional indirect ophthalmoscope, camera, and indirect lens, may be utilized to obtain accurate photographs of the retina, the fundus and other parts of the eye or the like. Since the apparatus of the present invention adapts for such use the ophthalmoscope, camera and indirect lens ordinarily available without special purchases by the ophthalmologist, expensive instrumentation specially designed for retina photography becomes unnecessary. Additionally, the apparatus is relatively lightweight and balanced allowing the same to be hand-held and truly portable.

Briefly, the invention is a portable apparatus for use in photographing the eye or the like, comprising a first mounting means for mounting an optical image forming means for forming an image of an object to be photographed, a second mounting means for mounting a camera in position to photograph such image, and a support means for holding the first and second mounting means in position to place such camera and image forming means in optical alignment. Other features of the invention include a mount to facilitate positioning of the viewing sight of an indirect ophthalmoscope in optical alignment to view the eye and to illuminate the eye for viewing and/or photographing purposes as well as to help steady the entire apparatus, a beam splitter for permitting simultaneous illuminating, viewing and photographing of the eye, and a handle to facilitate manually holding the entire apparatus in position for photographing the eye.

According to one embodiment the camera viewfinder is used to view the observed image to facilitate focusing and the light source from the indirect ophthalmoscope to illuminate the object to be photographed.

The words "eye", "retina" and "fundus" may be used interchangeably herein, all being representative of an object intended to be photographed.

With the foregoing and following detailed disclosure in mind, a primary object of the invention is to facilitate photographing parts of the eye, and particularly the retina and/or fundus.

Another object is to minimize the cost for equipment to photograph parts of the eye.

An additional object is to enable the use of equipment usually on-hand in the office of an ophthalmologist or otherwise relatively conveniently available for photographing parts of the eye.

A further object is to provide a portable stand, and especially one that may be readily hand-held, for use in photographing parts of the eye.

Still another object is to improve the portability of equipment for accurately photographing parts of the eye.

These and other objects and advantages of the present invention will become more apparent as the following description proceeds.

To the accomplishment of the foregoing and related ends, the invention, then, comprises the features hreinafter fully described in the specification and particularly pointed out in the claims, the following description and the annexed drawing setting forth in detail a certain illustrative embodiment of the invention, this being indicative, however, of but one of the various ways in which the principles of the invention may be employed.

BRIEF DESCRIPTION OF THE DRAWING

In the annexed drawing:

FIG. 1 is an isometric view of a hand-held retina photographing apparatus in accordance with the present invention;

FIG. 2 is a fragmentary section view illustrating the adjustment mechanism for the indirect lens;

FIG. 3 is a side view of an apparatus in accordance with the invention illustrating the manner of use thereof; and FIG. 4 is a side view of the preferred embodiment and best mode of the invention.

DESCRIPTION OF THE PREFERRED EMBODIMENT

Referring now in detail to the drawing, wherein like reference numerals designate like parts in the several figures, a hand-held retina photographing apparatus in accordance with the present invention is generally indicated at 1. The apparatus 1 includes a portable support 2 having a horizontal support platform 3, a downwardly depending camera mounting arm 4, a handle 5, a movable mounting bracket 6 for a conventional indirect lens, and an alignment mounting bracket 7 for receiving and holding the viewing sight 8 of a conventional indirect ophthalmoscope 9 in position relative to the portable support 2.

The support platform 3 preferably is formed of sheet metal having a top surface 10 with a plurality of cutouts or openings 11 for minimizing the material and, thus, the weight of the apparatus 1. From the top surface 10 flanges 12 depend downwardly to give the portable support 2 added strength and rigidity.

The camera mounting arm 4 is welded or otherwise securely fastened to the support platform 3 and is relatively rigid to provide with respect to the latter a fixed mounting location for a conventional camera 13. A wing nut or other conventional fastening mechanism 14 secures the camera 13 to the mounting arm 4, and a bent-over plate support 15, which may be part of the mounting arm 4, provides additional security of the camera connection to the latter.

A conventional indirect lens 20, which may be, for example, a 20 diopter lens, is mounted in the movable bracket 6 relative to the support platform 3 proximate the forward or leading edge 22 thereof. It is the purpose of the indirect lens 20 to form in conventional manner a focused image of the object being viewed using the apparatus 1, and it is the purpose of the camera 13 to photograph such image. To that end, then, the lens 20 ordinarily forms such image at a location between the lens 20 and the camera 13; such image may be formed, when using a 20 diopter lens, approximately 5 cm. from the lens between the latter and the camera, for example, at an image location or image plane designated 23. The movable bracket 6 includes a screw thread 24 which extends down through an elongate slot 25 in the platform 3. A wing nut and washer 26, 27 or other convenient conventional securing means may be loosened to permit sliding of the lens 20 and bracket 6 along the path of the slot 25 and may be tightened to secure the lens and bracket at a fixed location. If desired, conventional alignment tracks, or the like, may be provided to maintain the optical axis of the lens 20 parallel to the optical axis 30 of the apparatus 1 and, accordingly, the linear extent of the support platform 3 as the lens 20 may be moved.

A large cut-out opening 31 in the top surface 10 of the support platform 3 permits reflecting of the image formed by the indirect lens 20 to the camera 13 via a one-way mirror, beam splitter, or the like 32. The beam splitter 32 is mounted in a frame 33, which is held in fixed position relative to the support platform 3 by a mounting plate 34 fastened, for example, by welding thereto. Preferably the plane of the beam splitter 32 intersects that of the top surface 10 of the support platform 3 at about a 45° angle in order to direct some of the light from the image at the image location 23 along the optical axis 30', which is perpendicular to axis 30, into the camera lens 35 and to pass some of the light from such image along the optical axis 30 toward the back end 36 of the support platform 3 for pick-up by the viewing sight 7 and observation by the ophthalmologist.

The handle 5 is mounted approximately at the horizontal center of mass of the apparatus 1 in order to facilitate maintaining the balance thereof during use. A trigger 37 in the handle may be connected via a cable 38 to the camera 13 for a remote shutter release, thus further facilitating use of the apparatus 1.

If desired, the apparatus 1 may be used to photograph the retina by viewing the image formed at the image location 23 directly through the camera viewfinder, not shown. However, coordinating adjustment of the indirect lens 20 and the focusing mechanism, not shown, of the camera 13 becomes relatively difficult and relatively inaccurate in view of the lack of resolution in the camera viewfinder itself, the lack of a concentrated light source for illuminating the retina, and movement by the patient.

Ordinarily the viewing sight 8 of a conventional indirect ophthalmoscope 9 includes internally optical elements, such as mirrors, prisms, beam combiners, beam splitters, lenses, etc., all of which are collectively referred to hereinafter as the ophthalmoscope optics, not shown. The ophthalmoscope 9 typically includes its own light source 40 which via the ophthalmoscope optics and opening 41 in the viewing sight 8 provides a concentrated light beam for illuminating the retina or other object intended to be viewed. The opening 41 also receives light from such object, and particularly part of the light from the image at the image location 23, and the ophthalmoscope optics provides such image for binocular type viewing by the ophthalmologist.

In the usual case the viewing sight 8 is of rectangular or similar three dimensional form, such as that illustrated particularly in FIG. 1, and, accordingly, the alignment mounting bracket 7 includes two Z-shape legs 42, 43 for cooperating with the end surface 44 of the support platform 3 to hold the viewing sight 8 in relatively fixed position, but easily removable, with respect to the support platform 3. Preferably the spacing between the legs 42, 43 is such that they cooperate with the vertically extending housing portion 45 of the light source 40 to align the opening 41 with the optical axis 30 such that the opening 41, optical axes 30, 30', and optical axis of the indirect lens 20 preferably coincide in the manner illustrated in the drawing. Equivalent means also may be used to facilitate and to assure alignment of the ophthalmoscope and the various axes. Depending lips or edges 46 or other clip-like holders further may be employed to hold the viewing sight 8 in place; if desired the legs 42, 43, then, may be resilient to facilitate coupling and uncoupling of the viewing sight.

To use the hand-held retina photographing apparatus 1, an ophthalmologist may attach his own camera 13 to the camera mounting arm 4, may mount his own indirect lens in the movable bracket 21 and may use his own indirect ophthalmoscope 9 positioning the same in the alignment mounting bracket 7 to use light from the light source 40 for illuminating the retina and to view the latter through the viewing sight 8. In the usual practice, the ophthalmologist previously will have adjusted the position of the indirect lens 20 and the focusing apparatus of the camera 13 with accuracy, say with respect to a fixed object, so that when the image viewed through the viewing sight 8, namely that at the image location 23, is in focus to the ophthalmologist, it also is in focus, for example at the focal plane, with respect to the camera.

The ophthalmologist dons the indirect ophthalmoscope 9, in the manner illustrated, for example, in FIG. 3, and places the viewing sight 8 in the alignment mounting bracket 7 of the apparatus 1. Then, the ophthalmologist sights through the binocular optics of the viewing sight 8, while manually holding the handle 5. Using both the head and hand of the ophthalmologist to support the apparatus 1, the latter may be maintained in extremely stable position. Light from the light source 40 exits the opening 41 and passes through the beam splitter 32 and indirect lens 20 to illuminate the patient's eye, and the ophthalmologist may move the apparatus 1 until the area of the patient's eye intended to be photographed is brought into accurate alignment and focus. The trigger 37 is squeezed, then, to operate the camera 13 thereby photographing the viewed object.

The indirect ophthalmoscope 9 and indirect lens 20 ordinarily are typical instruments found in the office of an ophthalmologist, and a conventional camera also frequently is found in such an office or, at least, can be purchased at relatively minimal cost, especially in comparison to the specialized cameras used in the past for photographing the retina. Therefore, it will be appreciated that to equip an office with the equipment necessary to obtain accurate photographs of the retina, the ophthalmologist need only purchase the hand-held retina photographing apparatus 1 in accordance with the invention, which, too, may be relatively inexpensive in comparison to the specialized optical equipment used in the past for retina photography.

It will be appreciated that various modifications may be employed in connection with the apparatus 1, in accordance with the spirit and scope of the invention. For example, a separate light source may be built into the apparatus 1 to illuminate the retina independently of the light source 40. Such light source may be mounted in a manner similar to that of the camera 13 and may use a further beam splitter to direct light along the optical axis 30 for illuminating the retina. Other modifications may include, for example, a rack and pinion position adjusting mechanism for the indirect lens 20 and an adjustable alignment mounting bracket 7 to accommodate a variety of viewing sights 8 to obtain sighting along the optical axis 30. Moreover, if desired, a tripod-like or other portable stand may be provided for attachment, for example to the bottom of the handle 5, to facilitate steadying the apparatus 1.

The preferred embodiment and best mode of the invention is shown in FIG. 4, wherein primed reference numerals designate parts corresponding to those shown in FIGS. 1–3 and designated by unprimed reference numerals. In the apparatus 1' the camera 13' is mounted on the top 10' of support 2' for direct viewing of the patient by the doctor through viewfinder 50 and facile focusing and the indirect ophthalmoscope viewing sight 8' is mounted in bracket 7' on arm 4' primarily for illuminating the patient's eye. Set up and use of the apparatus 1' is similar to that described above.

I claim:

1. A portable apparatus for use in photographing an eye or the like, comprising first mounting means for mounting an optical image-forming means for forming an image of an object to be photographed, second mounting means for mounting a camera in position to photograph such an image, support means for holding said first and second mounting means in position to place such camera and image-forming means in optical alignment, said support means including an elongate support platform of length appropriate for viewing from one end the eye of a patient placed at the opposite end and for photographing such eye, handle means for facilitating manual holding of said support platform in position with respect to such an object to be photographed, and alignment mounting bracket means for holding at least part of an indirect ophthalmoscope in aligned position relative to said support means to direct light toward such optical image-forming means to illuminate such object to be photographed.

2. The apparatus of claim 1, further comprising a remote trigger release means coupled to said handle means for remotely releasing the shutter of a camera.

3. A portable apparatus for use in photographing an eye or the like, comprising first mounting means for mounting an optical image-forming means for forming an image of an object to be photographed, second mounting means for mounting a camera in position to photograph such an image, support means for holding said first and second mounting means in position to place such camera and image-forming means in optical alignment, and alignment mounting bracket means for holding at least part of an indirect ophthalmoscope in aligned position relative to said support means to view such image formed by such optical image-forming means.

4. The apparatus of claim 3, said first mounting means including means for adjusting the position thereof relative to said support means.

5. The apparatus of claim 3, further comprising splitter means for splitting light from such image formed by such image forming means, and splitter mounting means for mounting said splitter means relative to said support means for directing one portion of light from such image to such camera and another portion of light from such image to a viewing station.

6. The apparatus of claim 5, further comprising further mounting means for mounting said support means relative to an indirect ophthalmoscope viewing station having a light source, said splitter means and such image-forming means being positioned on said support means to direct light from such light source to illuminate the eye and to direct another portion of light from such image to such indirect ophthalmoscope.

7. The apparatus of claim 6, said splitter means comprising a half silvered mirror.

8. The apparatus of claim 6, said image-forming means comprising an indirect lens means for forming an image of that portion of the eye intended to be photographed, and said first mounting means including means for adjusting the position thereof relative to said support means.

9. The apparatus of claim 3, said support means comprising an elongate support platform, and said second mounting means comprising a mounting arm attached to and depending from said support platform and means for holding a camera to said mounting arm.

10. The apparatus of claim 3, said support means comprising an elongate support platform, and said mounting means for mounting said support means relative to an indirect ophthalmoscope including alignment bracket means cooperative with a portion of said support platform at an end thereof for removably holding the viewing sight of an indirect ophthalmoscope in secure position with respect to an optical axis of such optical image-forming means and such camera.

11. The apparatus of claims 1 or 3, further comprising means for passing to such camera light from such image formed by such image-forming means while also directing light from such indirect ophthalmoscope toward such object to be photographed, and mounting means for mounting said means for passing relative to said support means.

12. The apparatus of claim 11, said means for passing comprising a half silvered mirror.

13. The apparatus of claim 11, said image-forming means comprising an indirect lens means for forming an image of that portion of the eye intended to be photographed, and said first mounting means including means for adjusting the position thereof relative to said support means.

* * * * *